(12) United States Patent
Liao (10) Patent No.: US 12,109,028 B2
(45) Date of Patent: Oct. 8, 2024

(54) METHOD OF MAKING AN ELECTRODE ON A COVER GLASS OF A WEARABLE ELECTRONIC DEVICE

(71) Applicant: Google LLC, Mountain View, CA (US)

(72) Inventor: Yehua Liao, Shenzhen (CN)

(73) Assignee: GOOGLE LLC, Mountain View, CA (US)

( * ) Notice: Subject to any disclaimer, the term of this patent is extended or adjusted under 35 U.S.C. 154(b) by 0 days.

(21) Appl. No.: 18/010,348

(22) PCT Filed: Mar. 7, 2022

(86) PCT No.: PCT/CN2022/079555
§ 371 (c)(1),
(2) Date: Dec. 14, 2022

(87) PCT Pub. No.: WO2023/168561
PCT Pub. Date: Sep. 14, 2023

(65) Prior Publication Data
US 2023/0277108 A1    Sep. 7, 2023

(51) Int. Cl.
*A61B 5/256*     (2021.01)
(52) U.S. Cl.
CPC ...... *A61B 5/256* (2021.01); *A61B 2562/0209* (2013.01); *A61B 2562/125* (2013.01); *Y10T 29/49002* (2015.01)
(58) Field of Classification Search
CPC .... A61B 2560/0468; A61B 2562/0209; A61B 2562/125; A61B 5/256; A61B 5/681
See application file for complete search history.

(56) References Cited

U.S. PATENT DOCUMENTS 7,463,734 B2 * 12/2008 Tolbert .............. B32B 17/10137
455/575.1
9,276,043 B2    3/2016 Fujii et al.
(Continued)

FOREIGN PATENT DOCUMENTS

CN         103193397         7/2013
JP         2016/046347       4/2016

OTHER PUBLICATIONS

International Search Report and Written Opinion for Application No. PCT/CN2022/079555, mailed Nov. 29, 2022, 9 pages.
(Continued)

*Primary Examiner* — Minh N Trinh
(74) *Attorney, Agent, or Firm* — DORITY & MANNING P.A.

(57) ABSTRACT

A method for forming an electrode is provided. The method includes removing portion(s) of a removable protective film to produce a removable protective film element having a first defined shape; positioning the removable protective film element on a first portion of a cover glass such that the first portion has the first defined shape; defining a second portion of the cover glass based at least in part on positioning the removable protective film element on the first portion, the second portion having a second defined shape; depositing a metal material on the second portion and/or the removable protective film element; removing portion(s) of the metal material to form electrode(s) on the second portion; and/or removing the removable protective film element from the first portion to produce the electrode(s) formed on the cover glass such that the cover glass and/or the electrode(s) have defined attribute(s).

11 Claims, 8 Drawing Sheets

(56) References Cited

U.S. PATENT DOCUMENTS

| | | | |
|---|---|---|---|
| 10,698,259 B2* | 6/2020 | Son | G02F 1/133606 |
| 10,729,347 B1 | 8/2020 | Schleicher | |
| 2008/0023737 A1 | 1/2008 | Hwang et al. | |
| 2015/0241689 A1 | 8/2015 | Sakai et al. | |
| 2015/0301644 A1 | 10/2015 | Walley | |
| 2021/0066640 A1 | 3/2021 | Shin et al. | |
| 2022/0022794 A1 | 1/2022 | Jeong et al. | |
| 2022/0265197 A1 | 8/2022 | Tan et al. | |
| 2023/0190193 A1 | 6/2023 | Lee et al. | |
| 2023/0277108 A1* | 9/2023 | Liao | A61B 5/256 |

OTHER PUBLICATIONS

Extended European Search Report for Application No. EP 22868451.0, mailed Feb. 9, 2024, 9 pages.

* cited by examiner

METHOD OF MAKING AN ELECTRODE ON A COVER GLASS OF A WEARABLE ELECTRONIC DEVICE

FIELD

The present disclosure relates generally to wearable computing devices, and more particularly, use of a removable protective film to form a conductive region on a cover glass of a wearable computing device.

BACKGROUND

Currently, conductive regions (e.g., electrodes, sensors) are formed on a wearable computing device using a material deposition process such as, for example, a physical vapor deposition (PVD) process to deposit a conductive material (e.g., metal) on a cover glass of the wearable computing device. Portions of the deposited material are then removed using a material removal process such as, for instance, an etching process (e.g., laser etching) to form the final conductive region such that it has a certain shape (e.g., a certain geometry and/or profile) and/or certain aesthetic attributes (e.g., color, reflection intensity, texture, finish).

SUMMARY

Aspects and advantages of embodiments of the present disclosure will be set forth in part in the following description, or can be learned from the description, or can be learned through practice of the embodiments.

According to an example embodiment, a method to form an electrode on a cover glass of a wearable computing device can include removing one or more portions of a removable protective film to produce a removable protective film element having a first defined shape. The method can further include positioning the removable protective film element on a first portion of the cover glass such that the first portion of the cover glass has the first defined shape. The method can further include defining a second portion of the cover glass based at least in part on positioning the removable protective film element on the first portion of the cover glass. The second portion of the cover glass can have a second defined shape. The method can further include depositing a metal material on at least one of the second portion of the cover glass or the removable protective film element. The method can further include removing one or more portions of the metal material to form the electrode on the second portion of the cover glass. The method can further include removing the removable protective film element from the first portion of the cover glass to produce the electrode formed on the cover glass of the wearable computing device such that at least one of the cover glass or the electrode has one or more defined attributes.

According to another example embodiment, a wearable computing device can include one or more controllers. The wearable computing device can further include one or more memory devices that can store instructions that, when executed by the one or more controllers, can cause the wearable computing device to perform one or more operations. The wearable computing device can further include a cover glass having a first removable film defined portion and a second removable film defined portion. The wearable computing device can further include an electrode disposed on the second removable film defined portion of the cover glass. The electrode can be coupled to at least one of the one or more controllers. At least one of the cover glass or the electrode can have one or more defined attributes.

According to another example embodiment, a method to form a conductive region on a cover glass of a wearable computing device can include forming a removable protective film element on a first portion of the cover glass. The removable protective film element can have a first defined shape. The method can further include forming a conductive region on a second portion of the cover glass that is different from and proximate to the first portion of the cover glass. The second portion and the conductive region can have a second defined shape. The method can further include removing the removable protective film element from the first portion of the cover glass to produce the conductive region formed on the cover glass of the wearable computing device such that at least one of the cover glass or the conductive region has one or more defined attributes that are defined based at least in part on at least one of formation of the removable protective film element on the first portion of the cover glass, formation of the conductive region on the second portion of the cover glass, or removal of the removable protective film element from the cover glass.

Other aspects of the present disclosure are directed to various systems, apparatuses, non-transitory computer-readable media, user interfaces, and electronic devices.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to one of ordinary skill in the art is set forth in the specification, which makes reference to the appended figures, in which.

DETAILED DESCRIPTION

Reference now will be made in detail to embodiments of the present disclosure, one or more examples of which are illustrated in the drawings. Each example is provided by way of explanation of the present disclosure, not limitation of the present disclosure. In fact, it will be apparent to those skilled in the art that various modifications and variations can be made in the present disclosure without departing from the scope or spirit of the disclosure. For instance, features illustrated or described as part of one embodiment can be used with another embodiment to yield a still further embodiment. Thus, it is intended that the present invention covers such modifications and variations as come within the scope of the appended claims and their equivalents.

As referenced herein, the term "entity" refers to a human, a user, an end-user, a consumer, a computing device and/or program (e.g., a processor, computing hardware and/or software, an application, etc.), an agent, a machine learning (ML) and/or artificial intelligence (AI) algorithm, model, system, and/or application, and/or another type of entity that can implement and/or facilitate implementation of one or more embodiments of the present disclosure as described herein, illustrated in the accompanying drawings, and/or included in the appended claims. As referenced herein, the terms "or" and "and/or" are generally intended to be inclusive, that is (i.e.), "A or B" or "A and/or B" are each intended to mean "A or B or both." As referred to herein, the terms "first," "second," "third," etc. can be used interchangeably to distinguish one component or entity from another and are not intended to signify location, functionality, or importance of the individual components or entities. As used herein, the use of the wan "about" and/or "approximate" in conjunction with a numerical value refers to within 10% of the indicated numerical value. As referenced herein, the terms "couple," "couples," "coupled," and/or "coupling" refer to chemical coupling (e.g., chemical bonding), communicative coupling, electrical and/or electromagnetic coupling (e.g., capacitive coupling, inductive coupling, direct and/or connected coupling, etc.), mechanical coupling, operative coupling, optical coupling, and/or physical coupling.

Overview

Example aspects of the present disclosure are directed to the use of a removable protective film to form a conductive region on a cover glass of a wearable computing device. Currently, conductive regions (e.g., electrodes, sensors) are formed on a wearable computing device using a material deposition process such as, for example, a physical vapor deposition (PVD) process to deposit a conductive material (e.g., metal) on a cover glass of the wearable computing device and a material removal process such as, for instance, an etching process (e.g., laser etching) to remove portions of the conductive material to form a conductive region.

A problem with using an etching process to remove portions of the conductive material is that it is difficult to form the conductive region on the cover glass such that the cover glass is not damaged in the process and such that the conductive region and/or the cover glass satisfy one or more design criteria. For instance, using an etching process to remove portions of the conductive material from the cover glass can damage the cover glass to the point that it is no longer transparent enough to satisfy a certain design criterion. As another example, it is difficult to use an etching process to remove portions of the conductive material such that the conductive region ultimately has a certain profile (e.g., curved, sloped), a certain geometry (e.g., U-shaped), certain edges (e.g., rounded edges, flat edges), a certain location (e.g., a certain location relative to the cover glass), certain dimensions, and/or certain aesthetic features (e.g., color, reflection intensity, texture, finish).

Example methods according to one or more embodiments of the present disclosure can include using a removable protective film to form a conductive region (e.g., electrically conductive, thermally conductive) on a cover glass of a wearable computing device. For instance, example methods according to one or more embodiments of the present disclosure can include using a removable protective film to form an electrode on a cover glass of a wearable computing device such that the cover glass and/or the electrode include one or more defined attributes. For example, one or more example methods according to one or more embodiments of the present disclosure can include using a removable protective film to form an electrode on a cover glass of a wearable computing device such that the cover glass and/or the electrode include a certain dimension, a certain profile (e.g., curved, sloped), a certain geometry (e.g., U-shaped, channel shaped), one or more certain edges (e.g., rounded edge(s), flat edge(s)), a certain location (e.g., a certain location of the electrode relative to the cover glass), a certain aesthetic feature (e.g., color, reflection intensity, texture, finish), and/or another defined attribute.

In some embodiments, one or more methods according to embodiments of the present disclosure can include using a removable protective film to form an electrode such as, for instance, a sensor, a biometric sensor, a fingerprint sensor, a temperature sensor, a humidity sensor, a light sensor, a pressure sensor, an image sensor, a microphone, a photoplethysmogram (PPG) sensor, an electrodermal activity sensor, and/or another sensor on a cover glass of a wearable computing device. In these or other embodiments, one or more methods according to embodiments of the present disclosure can include using a removable protective film to form an electrode on a cover glass of a wearable computing device such as, for instance, a smartwatch, a personal health monitoring device, a biometric tracking device, a biometric monitoring device, a heart monitor, a fitness tracker, and/or another wearable computing device.

In one example embodiment, a method to form an electrode (e.g., a sensor) on a cover glass of a wearable computing device according to one or more embodiments can include removing one or more portions of a removable protective film to produce a removable protective film element (e.g., a piece or a unit of the removable protective film) having a first defined shape. For example, the method can include removing portion(s) of a removable protective film to produce a section, piece, or unit of the removable protective film that has the shape of a section of the cover glass that is to be protected during processing (e.g., during subsequent material deposition and/or removal process(es)). In some embodiments, the removable protective film element can include a polyethylene terephthalate (PET) material layer and an adhesive material layer disposed on a surface of the polyethylene terephthalate (PET) material layer.

In at least one embodiment, the method can include positioning the removable protective film element on a first portion of the cover glass such that the first portion of the cover glass has the first defined shape. For example, the method can include positioning the removable protective film element on the section of the cover glass that is to be protected such that the shape of the first portion of the cover glass is the same as that of the first defined shape of the removable protective film element. In embodiments where the removable protective film element includes a PET material layer having an adhesive material layer disposed thereon, the method can include positioning the removable protective film element on the first portion of the cover glass by coupling the PET material layer and the adhesive material layer to the first portion of the cover glass. In these or other embodiments, the PET material layer can be coupled to the first portion of the cover glass via the adhesive material layer.

In one or more embodiments, the method can include defining a second portion of the cover glass based at least in part on positioning the removable protective film element on the first portion of the cover glass, where the second portion of the cover glass can have a second defined shape. For example, the method can include defining the shape of the section of the cover glass where the electrode material is to be deposited by placing the removable protective film element on the first portion of the cover glass. In some embodiments, the second portion of the cover glass can be different from and/or proximate to the first portion of the cover glass. For instance, the first portion of the cover glass can have a substantially square or rectangular shape and can be located at the center of the cover glass. In this example, the second portion of the cover glass can have a substantially U-shaped or channel shaped configuration that can be located adjacent to and/or at least partially around the perimeter of the first portion of the cover glass. In at least one embodiment, the second portion of the cover glass can include and/or constitute two substantially U-shaped or channel shaped sections of the cover glass that are located adjacent to and/or at least partially around the perimeter of the first portion of the cover glass.

According to one or more embodiments, the method can include depositing a metal material on the second portion of the cover glass and/or the removable protective film element. For example, the method can include performing a material deposition process such as, for instance, a physical vapor deposition (PVD) process to deposit a metal material (e.g., an electrically and/or thermally conductive metal material) on the second portion of the cover glass and/or the removable protective film element. In some embodiments, the method can include performing a material deposition process such as, for instance, a PVD process to deposit the metal material on the second portion of the cover glass and an exposed surface (e.g., top surface) of the removable protective film element. In embodiments where the removable protective film element includes a PET material layer having an adhesive material layer that is disposed on the PET material layer and coupled to the first portion of the cover glass, the method can include performing a material deposition process such as, for instance, a PVD process to deposit the metal material on the second portion of the cover glass and an exposed surface (e.g., top surface) of the PET material layer.

In at least one embodiment, the method can include removing one or more portions of the metal material to form the electrode on the second portion of the cover glass. For example, the method can include performing a grinding process, an etching process (e.g., wet etching, thy etching, laser etching), a polishing process, a cleaning process (e.g., an ultrasonic cleaning process), and/or another material removal process to remove the one or more portions of the metal material to form the electrode on the second portion of the cover glass. In some embodiments, the method can include removing one or more portions of the metal material from the second portion of the cover glass and keeping at least some amount, if not all, of the metal material deposited on the removable protective film element (e.g., the metal material that was deposited on the removable protective film element during deposition of the metal material).

In at least one embodiment of the present disclosure, the method can include removing the removable protective film element from the first portion of the cover glass to produce the electrode formed on the cover glass of the wearable computing device such that the cover glass and/or the electrode include one or more defined attributes (e.g., one or more of the above-described attributes). For example, the method can include performing a peeling process (e.g., a tape peeling process), a polishing process, and/or a cleaning process (e.g., an ultrasonic cleaning process) to remove the removable protective film element from the first portion of the cover glass. In some embodiments, the method can include removing (e.g., via peeling, polishing, and/or ultrasonic cleaning) the removable protective film element, and a defined amount of the metal material disposed on the removable protective film element, from the first portion of the cover glass. For example, the method can include removing (e.g., via peeling, polishing, and/or ultrasonic cleaning) the removable protective film element, and all the metal material that was deposited on the removable protective film element during deposition of the metal material, from the first portion of the cover glass.

In embodiments where the removable protective film element includes a PET material layer having an adhesive material layer that is disposed on the PET material layer and coupled to the first portion of the cover glass, the method can include removing the PET material layer and the adhesive material layer from the first portion of the cover glass. For example, in these or other embodiments, the method can include performing a peeling process (e.g., a tape peeling process), a polishing process, and/or a cleaning process (e.g., an ultrasonic cleaning process) to remove the PET material layer and the adhesive material layer from the first portion of the cover glass. In these or other embodiments, the method can include performing such a peeling, polishing, and/or cleaning process to remove the PET material layer, the adhesive material layer, and all the metal material that was deposited on the PET material layer of the removable protective film element during deposition of the metal material, from the first portion of the cover glass.

In at least one embodiment of the present disclosure, one or more example methods described herein can be implemented to form an electrode (e.g., a sensor) on a cover glass of a wearable computing device using a removable protective film. In this or another embodiment, implementation of such example method(s) described herein can yield: a cover glass having a first removable film defined portion and a second removable film defined portion; and an electrode (e.g., a sensor) disposed on the second removable film defined portion of the cover glass. In this or another embodiment, the cover glass and/or the electrode can include one or more defined attributes such as, for instance, one or more of the above-described defined attributes. In some embodiments, a wearable computing device described herein can include such a cover glass having such first and second removable film defined portions and such an electrode disposed on the second removable film defined portion of the cover glass. In one or more embodiments, the wearable computing device can further include one or more controllers and one or more memory devices (e.g., non-transitory computer-readable storage media) that can store instructions that, when executed by the one or more controllers, can cause the wearable computing device to perform one or more operations. In at least one embodiment, the above-described electrode can be coupled (e.g., communicatively, electrically, operatively) to at least one of the one or more controllers. In some embodiments, the above-described electrode can include and/or constitute a sensor such as, for instance, a biometric sensor. In these embodiments, the wearable computing device can perform the one or more operations based at least in part on (e.g., in response to) data (e.g., biometric data) that can be captured by such a sensor.

Example aspects of the present disclosure provide several technical effects, benefits, and/or improvements in wearable computing device technology. For example, as described above, example methods according to one or more embodiments of the present disclosure can include using a removable protective film to form a sensor (e.g., a biometric sensor) on a cover glass of a wearable computing device. In these one or more embodiments, the removable protective film can protect the cover glass during subsequent processing and thereby reduce or eliminate damage to the cover glass that can otherwise occur during, for instance, subsequent material deposition (e.g., PVD) and/or material removal processes (e.g., etching, grinding, polishing, cleaning).

Further, as described above, example methods according to one or more embodiments of the present disclosure can include using a removable protective film to form a sensor (e.g., a biometric sensor) on a cover glass of a wearable computing device such that the cover glass and/or the sensor include a certain dimension, a certain profile (e.g., curved, sloped), a certain geometry (e.g., U-shaped, channel shaped), one or more certain edges (e.g., rounded edge(s), flat edge(s)), a certain location (e.g., a certain location of the sensor relative to the cover glass), a certain aesthetic feature (e.g., color, reflection intensity, texture, finish), and/or another defined attribute. In these one or more embodiments, by facilitating formation of such a sensor and/or cover glass having such attribute(s), the present disclosure can improve the accuracy of data (e.g., biometric data) captured by the sensor, which can improve the user experience of an entity (e.g., a human) using a wearable computing device having such a sensor. In these one or more embodiments, by improving the accuracy of data captured by such a sensor, the present disclosure can also improve the performance and/or efficiency, as well as reduce operational costs of the wearable computing device and/or one or more components thereof. For instance, by improving the accuracy of data captured by such a sensor, the present disclosure can improve the processing performance and/or processing efficiency, as well as reduce computational costs of one or more processors (e.g., controller(s)) of the wearable computing device.

With reference now to the Figures, example embodiments of the present disclosure will be discussed in further detail.

Example Devices, Systems, and Methods

Figure 1:
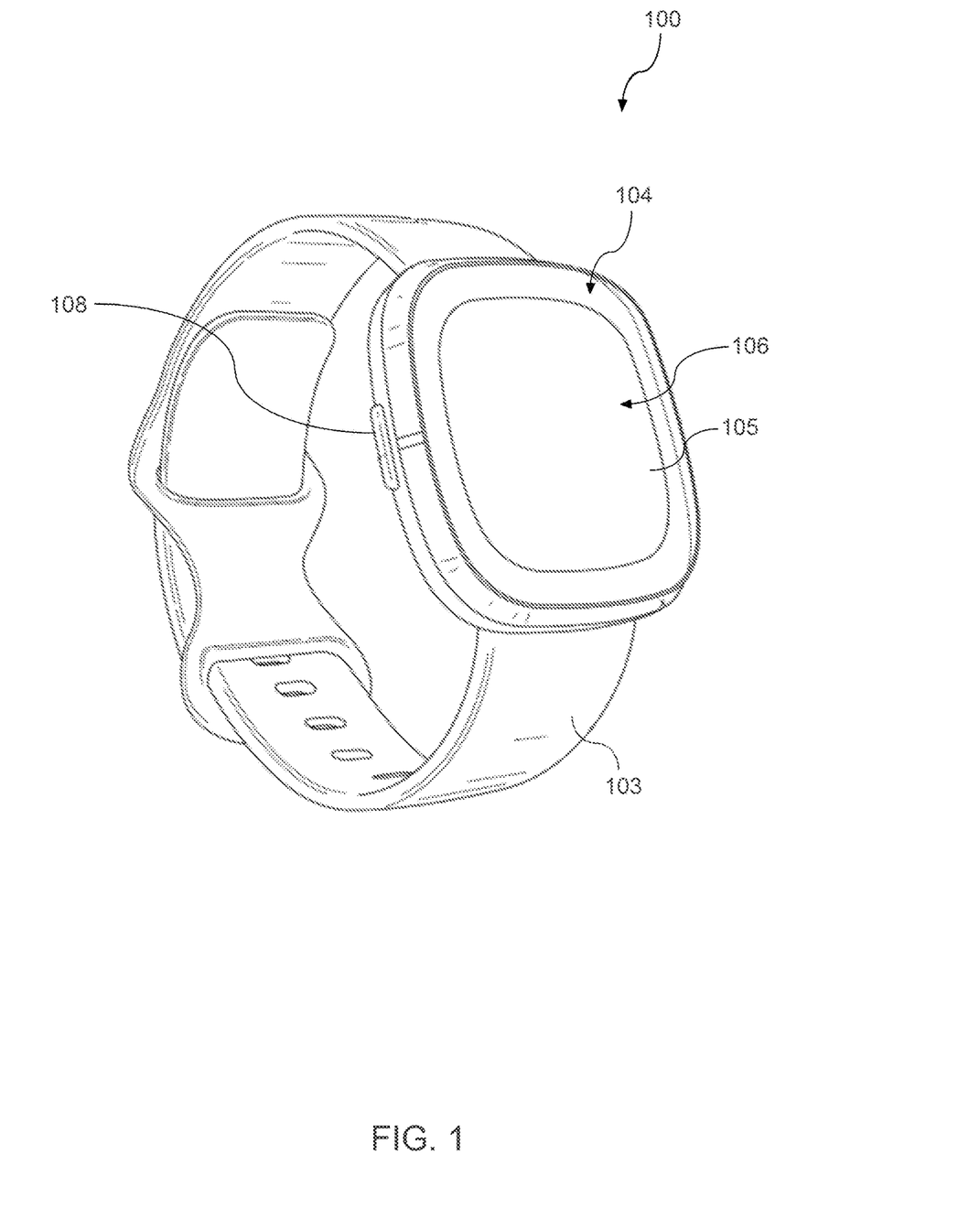
FIG. 1 illustrates a front perspective view of an example, non-limiting wearable computing device according to one or more embodiments of the present disclosure.
Figure 2:
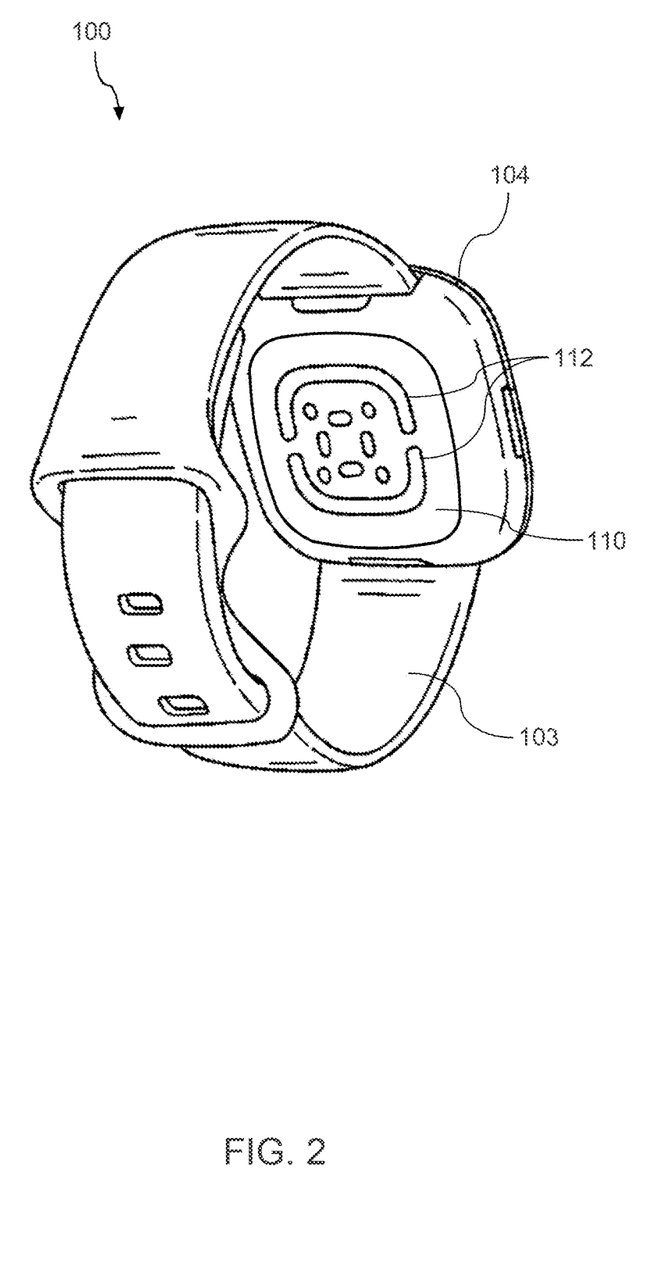
FIG. 2 illustrates a rear perspective view of the example, non-limiting wearable computing device of FIG. 1.
Figure 3:
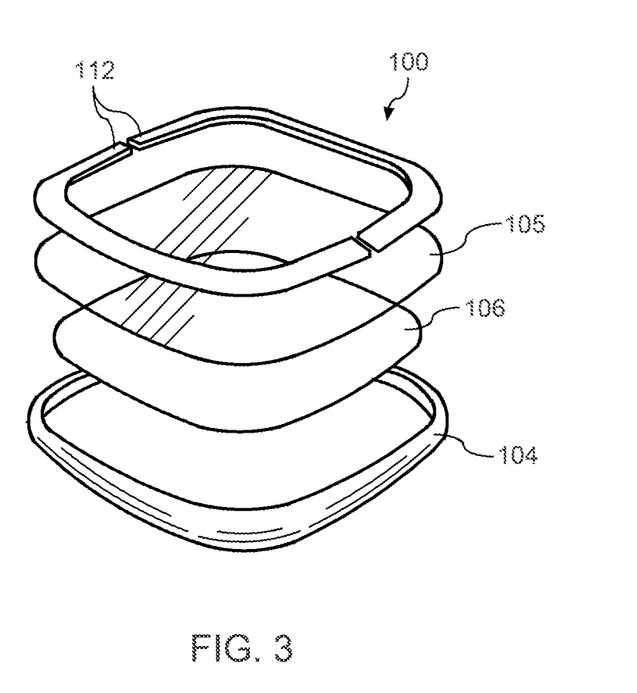
FIG. 3 illustrates an exploded view of example, non-limiting display components of the example, non-limiting wearable computing device of FIG. 1.

FIGS. 1, 2, and 3 illustrate various views of an example, non-limiting wearable computing device 100 and/or components thereof according to one or more embodiments of the present disclosure. FIG. 1 illustrates a front perspective view of wearable computing device 100 according to one or more embodiments of the present disclosure. FIG. 2 illustrates a rear perspective view of wearable computing device 100 according to one or more embodiments of the present disclosure. FIG. 3 illustrates an exploded view of example, non-limiting display components of wearable computing device 100 according to one or more embodiments of the present disclosure.

With reference to FIGS. 1, 2, and 3, in at least one embodiment of the present disclosure, wearable computing device 100 can include and/or constitute, for instance, a smartwatch, a personal health monitoring device, a biometric tracking device, a biometric monitoring device, a heart monitor, a fitness tracker, and/or another type of wearable computing device. In some embodiments, wearable computing device 100 can be worn, for instance, on a user's forearm like a wristwatch.

As illustrated in the example embodiment depicted in FIGS. 1, 2, and 3, wearable computing device 100 can include a wristband 103 that can secure wearable computing device 100 to, for instance, a user's forearm. In at least one embodiment, wearable computing device 100 can include an outer covering 105 and/or a housing 104 that can include one or more electronic components and/or devices of wearable computing device 100. In an embodiment, outer covering 105 can include and/or constitute a cover glass. In some embodiments, outer covering 105 can be constructed of, for instance, glass, polycarbonate, acrylic, and/or a similar material. In the example embodiment depicted in FIGS. 1, 2, and 3, wearable computing device 100 can include a pixelated electronic display 106 that can be arranged within housing 104 and/or viewable through outer covering 105. As shown in FIG. 1, wearable computing device 100 can also include one or more buttons 108 that can be implemented (e.g., engaged by a user) to activate one or more sensors (described below) of wearable computing device 100 to collect certain health data of a user (e.g., biometric data). In at least one embodiment, electronic display 106 can cover an electronics package (not shown), which can also be housed within housing 104.

As illustrated in the example embodiment depicted in FIGS. 1, 2, and 3, housing 104 of wearable computing device 100 can include a dorsal wrist-side face 110 that can be configured to sit against a dorsal wrist of a user when being worn by the user. In this example embodiment, housing 104 can also include at least one sensor 112 that can be positioned on dorsal wrist-side face 110 of housing 104 such that sensor(s) 112 maintain skin contact with a user when being worn on the user's wrist.

In some embodiments, sensor(s) 112 can include and/or constitute an electrode and/or a conductive region of wearable computing device 100. In one or more embodiments, sensor(s) 112 can be configured to capture and/or measure various biometric parameters of the user. For example, in at least one embodiment, sensor(s) 112 can include and/or constitute a biometric sensor, a fingerprint sensor, a temperature sensor, a humidity sensor, a light sensor, a pressure sensor, an image sensor, a microphone, a photoplethysmogram (PPG) sensor, an electrodermal activity (EDA) sensor, and/or another sensor. In some embodiments, housing 104 can include one or more additional sensors such as, for instance, an additional image sensor, an additional biometric sensor, an additional fingerprint sensor, an additional temperature sensor, an additional humidity sensor, an additional light sensor, an additional pressure sensor, an additional microphone, an additional PPG sensor, an additional FDA sensor, and/or another sensor.

As described in detail below with reference to the example embodiments illustrated in FIGS. 6, 7A, 7B, 8, and 9, in one or more embodiments, sensor(s) 112 can be formed on outer covering 105 using a removable protective film according to at least one embodiment of the present disclosure. For example, method 800 and/or method 900 described below with reference to FIGS. 8 and 9 can be implemented to &mu sensor(s) 112 on outer covering 105 as illustrated in FIGS. 7A and 7B. In at least one embodiment, sensor(s) 112 can be formed on outer covering 105 using a removable protective film such that sensor(s) 112 and/or outer covering 105 have one or more defined attributes. For instance, method 800 and/or method 900 can be implemented to form sensor(s) 112 on outer covering 105 using a removable protective film such that sensor(s) 112 and/or outer covering 105 have a defined dimension, a defined profile, a defined geometry, a defined edge, a defined location, a defined aesthetic feature of the cover glass and/or the electrode, and/or another defined attribute. For example, method 800 and/or method 900 can be implemented to form sensor(s) 112 on outer covering 105 using a removable protective film such that sensor(s) 112 and/or outer covering 105 have a certain dimension, a certain profile (e.g., curved, sloped), a certain geometry (e.g., U-shaped, channel shaped), one or more certain edges (e.g., rounded edge(s), flat edge(s)), a certain location (e.g., a certain location of sensor(s) 112 relative to outer covering 105), a certain aesthetic feature (e.g., color, reflection intensity, texture, finish), and/or another attribute.

Figure 4:
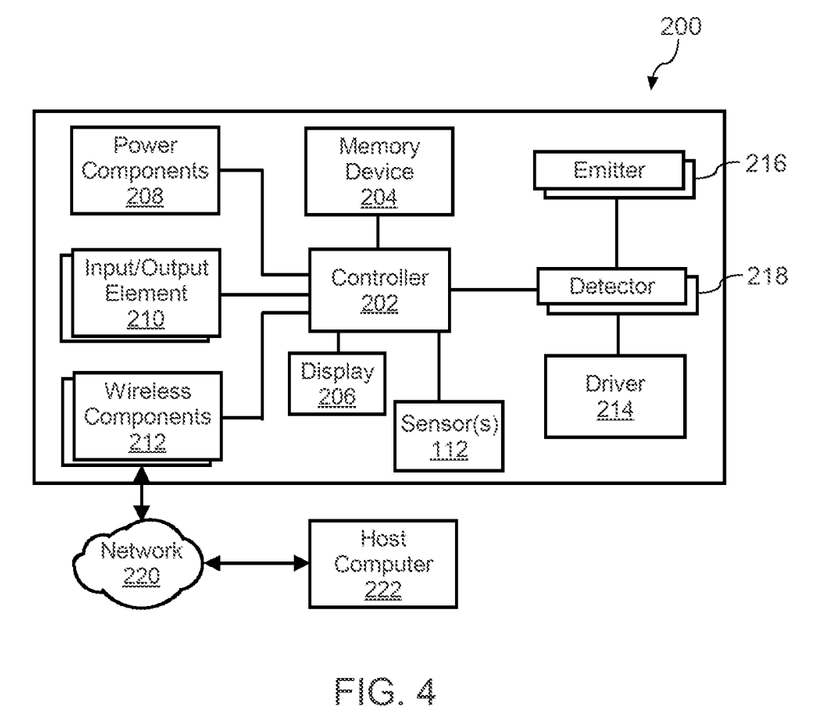
FIG. 4 illustrates a block diagram of an example, non-limiting computing system of the example, non-limiting wearable computing device of FIG. 1.

FIG. 4 illustrates a block diagram of an example, non-limiting computing system 200 of wearable computing device 100 according to one or more embodiments of the present disclosure. Computing system 200 and/or one or more components thereof can be utilized in accordance with various embodiments described herein. In particular, as shown in FIG. 4, computing system 200 can include at least one controller 202 that can be coupled to sensor(s) 112. In at least one embodiment, controller(s) 202 can include and/or constitute, for example, a central processing unit (CPU) or a graphics processing unit (GPU) that can be coupled to a memory device 204 of computing system 200. In this embodiment, controller(s) 202 can execute instructions that can be stored in memory device 204. For example, in an embodiment, memory device 204 can include and/or constitute one or more non-transitory computer-readable storage media such as, for instance, random-access memory (RAM), read only memory (ROM), dynamic random-access memory (DRAM), flash memory, and/or other non-transitory digital data storage (e.g., non-transitory computer-readable storage media). In at least one embodiment, memory device 204 can include a control program having one or more sequences of instructions which, when loaded from memory device 204 and executed by controller(s) 202, can cause controller(s) 202 and/or wearable computing device 100 to perform one or more operations according to example embodiments described herein.

In some embodiments, computing system 200 can include many types of memory, data storage, and/or computer-readable media, such as data storage for program instructions for execution by controller(s) 202 and/or any suitable processor. In some embodiments, the same or separate storage can be used by computing system 200 to store images and/or data. In some embodiments, a removable memory can be included with, coupled to, used by, and/or otherwise associated with computing system 200 to share information with other devices. In these or other embodiments, any number of communication approaches and/or protocols can be utilized by computing system 200 to share information with other devices.

In the example embodiment depicted in FIG. 4, computing system 200 can include pixelated electronic display 106. In this or another embodiment, pixelated electronic display 106 can include and/or constitute, for instance, a touch screen, an organic light emitting diode (OLED), a liquid crystal display (LCD), and/or another type of display. In some embodiments, wearable computing device 100 and/or computing system 200 can convey information via, for instance, an audio speaker, a projector, and/or by casting the display or streaming data to another device such as, for example, a mobile phone, where an application on the mobile phone can display the data.

As illustrated in the example embodiment depicted in FIG. 4, computing system 200 can include one or more wireless components 212 that can be operable to communicate with one or more electronic devices within a communication range of a wireless channel. For instance, the wireless channel can be any appropriate channel used to enable devices to communicate wirelessly such as, for example, Bluetooth®, cellular, near-field communication (NFC), Ultra-Wideband (UWB), or Wi-Fi channels. In at least one embodiment, computing system 200 can include one or more wired communication components (e.g., switch, network interface card (NIC), port, hardware, software).

In the example embodiment depicted in FIG. 4, computing system 200 can include one or more power components 208. For example, computing system 200 can include power component(s) 208 such as, for instance, a rechargeable battery that can be operable to be recharged via a plug-in protocol and/or via other approaches such as capacitive charging through proximity with a power mat or other such device. In some embodiments, computing system 200 can include at least one input/output (I/O) device 210 (denoted in FIG. 4 as "Input/Output Element 210") that can receive input from a user. For example, device(s) 210 can include a push button, a touch pad, a touch screen, a wheel, a joystick, a keyboard, a mouse, a keypad, and/or another I/O device or element a user can employ to input a command to computing system 200. In another embodiment, I/O device(s) 210 can be connected by a wireless infrared or Bluetooth® or other link as well. In some embodiments, computing system 200 can include a microphone or other audio capture element that can accept voice or other audio commands. For example, in particular embodiments, computing system 200 may not include any buttons, but instead might be controlled through a combination of visual and audio commands such that a user can control wearable computing device 100 without having to contact wearable computing device 100. In certain embodiments, I/O elements 210 can include one or more of sensor(s) 112 described herein, optical sensors, barometric sensors (e.g., altimeter), and/or another sensor.

As illustrated in the example embodiment depicted in FIG. 4, computing system 200 can include a driver 214 and at least some combination of one or more emitters 216 and one or more detectors 218 to capture and/or measure data associated with one or more metrics of, for instance, a user (e.g., a person) wearing wearable computing device 100. In some embodiments, this can involve at least one imaging element such as, for instance, one or more cameras that can capture images of the surrounding environment and/or can capture images of a user, people, and/or objects in the vicinity of wearable computing device 100. In some embodiments, the image capture element can include any appropriate technology such as, for instance, a charge-coupled device (CCD) or CCD image capture element having a sufficient resolution, focal range, and viewable area to capture an image of the user when the user is operating the device. Further image capture elements can also include depth sensors. Methods for capturing images using a camera element with a computing device are well known in the art and will not be discussed herein in detail. It should be understood that image capture can be performed using a single image, multiple images, periodic imaging, continuous image capturing, image streaming, and/or another image capture process. Further, computing system 200 can be operable to start and/or stop image capture such as, for instance, when receiving a command from a user, an application, and/or another device.

In some embodiments, emitters 216 and detectors 218 can be used, for instance, to obtain optical photoplethysmogram (PPG) measurements. Some PPG technologies rely on detecting light at a single spatial location, or adding signals taken from two or more spatial locations. Both of these approaches result in a single spatial measurement from which the heart rate (HR) estimate and/or other physiological metrics can be determined. In some embodiments, a PPG device employs a single light source coupled to a single detector (i.e., a single light path). Alternatively, a PPG device can employ multiple light sources coupled to a single detector or multiple detectors (i.e., two or more light paths). In other embodiments, a PPG device can employ multiple detectors coupled to a single light source or multiple light sources (i.e., two or more light paths). In some embodiments, the light source(s) can be configured to emit one or more of green, red, infrared (IR) light, as well as any other suitable wavelengths in the spectrum such as, for instance, long IR for metabolic monitoring. For example, a PPG device can employ a single light source and two or more light detectors each configured to detect a specific wavelength or wavelength range. In some embodiments, each detector can be configured and/or operable to detect a different wavelength or wavelength range from one another. In other embodiments, two or more detectors can be configured to detect the same wavelength or wavelength range. In yet another embodiment, one or more detectors can be configured and/or operable to detect a specific wavelength or wavelength range that can be different from one or more other detectors. In embodiments employing multiple light paths, the PPG device can determine an average of the signals resulting from the multiple light paths before determining an HR estimate or other physiological metrics.

In one embodiment, emitters 216 and detectors 218 can be coupled to controller(s) 202 directly or indirectly using, for instance, driver circuitry by which controller(s) 202 can drive emitters 216 and obtain signals from detectors 218. In the example embodiment depicted in FIG. 4, a host computer 222 can communicate with wireless networking components 212 of computing system 200 via one or more networks 220, which can include one or more local area networks, wide area networks, UWB, and/or internetworks using one or more terrestrial or satellite links. In some embodiments, host computer 222 can execute control programs and/or application programs that are configured to perform one or more of the operations described herein.

Figure 5:
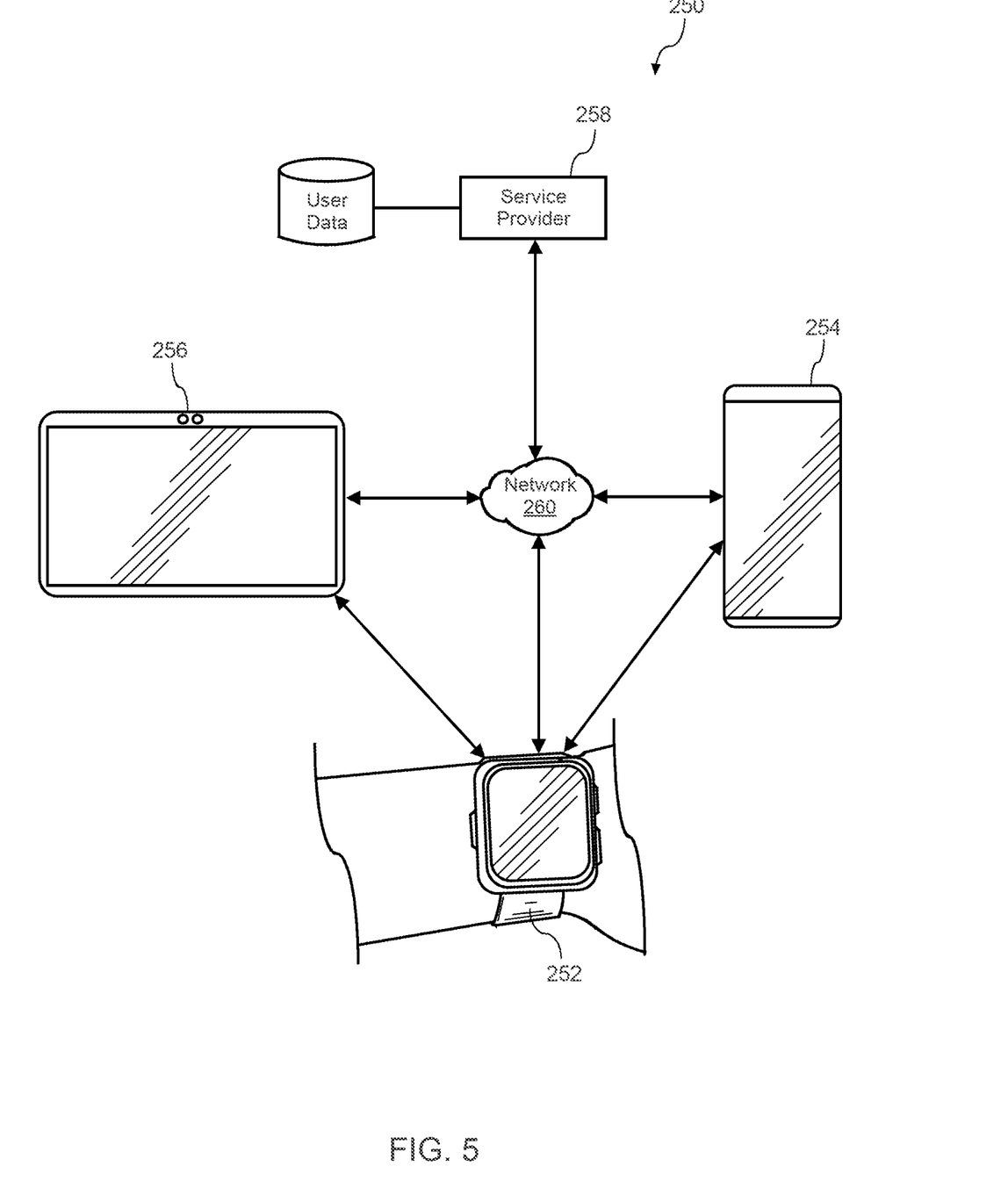
FIG. 5 illustrates a diagram of an example, non-limiting communication environment according to one or more embodiments of the present disclosure.

FIG. 5 illustrates a diagram of an example, non-limiting communication environment 250 according to one or more embodiments of the present disclosure. In some embodiments, communication environment 250 can facilitate implementation of one or more devices, systems, and/or operations according to one or more embodiments described herein. For example, as shown in FIG. 5, a user might have a number of different devices that are able to communicate using at least one wireless communication protocol. For instance, as shown in FIG. 5, the user might have a smartwatch 252 or fitness tracker (e.g., wearable computing device 100), which the user would like to be able to communicate with a smartphone 254 and/or a tablet computer 256. In some embodiments, the ability to communicate with multiple devices can enable a user to obtain information from smartwatch 252 (e.g., via data captured using a sensor on smartwatch 252) using, for instance, an application installed on smartphone 254 and/or tablet computer 256. In some embodiments, the user may want smartwatch 252 to communicate with a service provider 258, or other such entity, that can obtain and/or process data from smartwatch 252 and/or provide functionality that may not otherwise be available on smartwatch 252 or the applications installed on the individual devices. In some embodiments, as shown in FIG. 5, smartwatch 252 can communicate with service provider 258 through at least one network 260 such as, for instance, the Internet or a cellular network, or can communicate over a wireless connection such as, for example, Bluetooth® to one of the individual devices, which can then communicate over network(s) 260. There can be a number of other types of, or reasons for, communications in various embodiments.

In addition to being able to communicate, a user may also want the devices to communicate in a number of ways or with certain aspects. For example, the user may want communications between the devices to be secure, particularly where the data can include personal health data or other such communications. The device or application providers can also be required to secure this information in at least some situations. In one embodiment, the user may want the devices to communicate with each other concurrently, rather than sequentially. This may be particularly true where pairing may be required, as the user may prefer that each device be paired at most once, such that no manual pairing is required. The user may also desire the communications to be as standards-based as possible, not only so that little manual intervention is required on the part of the user but also so that the devices can communicate with as many other types of devices as possible, which is often not the case for various proprietary formats. A user may want to walk in a room with one device and have the device automatically communicate with another target device with little to no effort on the part of the user. In various conventional approaches, a device will utilize a communication technology such as Wi-Fi to communicate with other devices using wireless local area networking (WLAN). Smaller or lower capacity devices, such as many Internet of Things (IoT) devices, instead utilize a communication technology such as Bluetooth®, and in particular Bluetooth Low Energy (BLE) which has very low power consumption.

In further embodiments, communication environment 250 illustrated in the example embodiment depicted in FIG. 5 can enable data to be captured, processed, and/or displayed in a number of different ways. For example, data can be captured using sensors on smartwatch 252, but due to limited resources on smartwatch 252, the data can be transferred to smartphone 254 or service provider 258 (or a cloud resource) for processing, and results of that processing can then be presented back to that user on smartwatch 252, smartphone 254, and/or another such device associated with that user, such as tablet computer 256. In at least some embodiments, a user may also be able to provide input such as health data using an interface on any of these devices, which can then be considered when making that determination.

Figure 6:
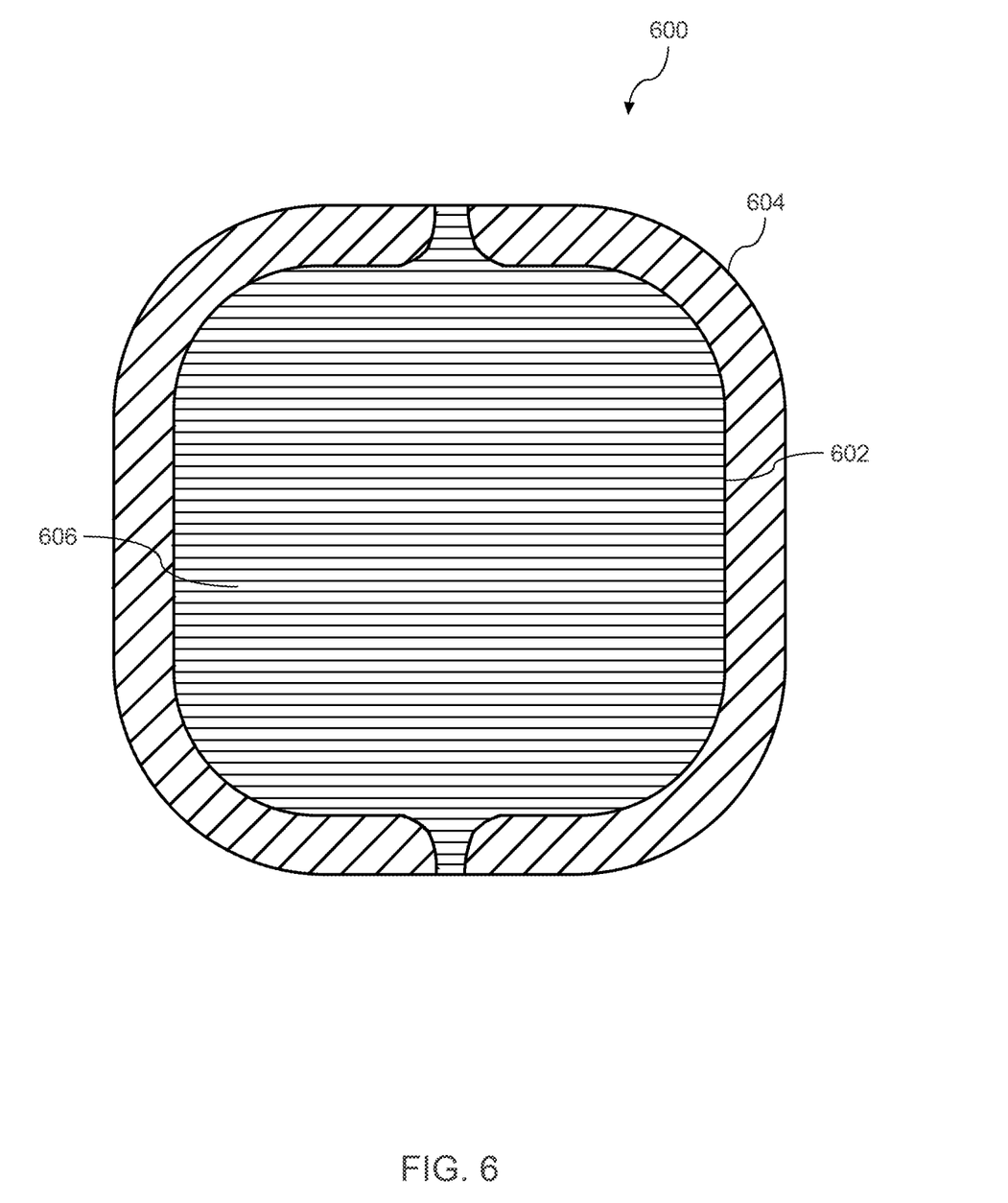
FIG. 6 illustrates a top view of an example, non-limiting outer covering of a wearable computing device according to one or more embodiments of the present disclosure.
Figure 7A:
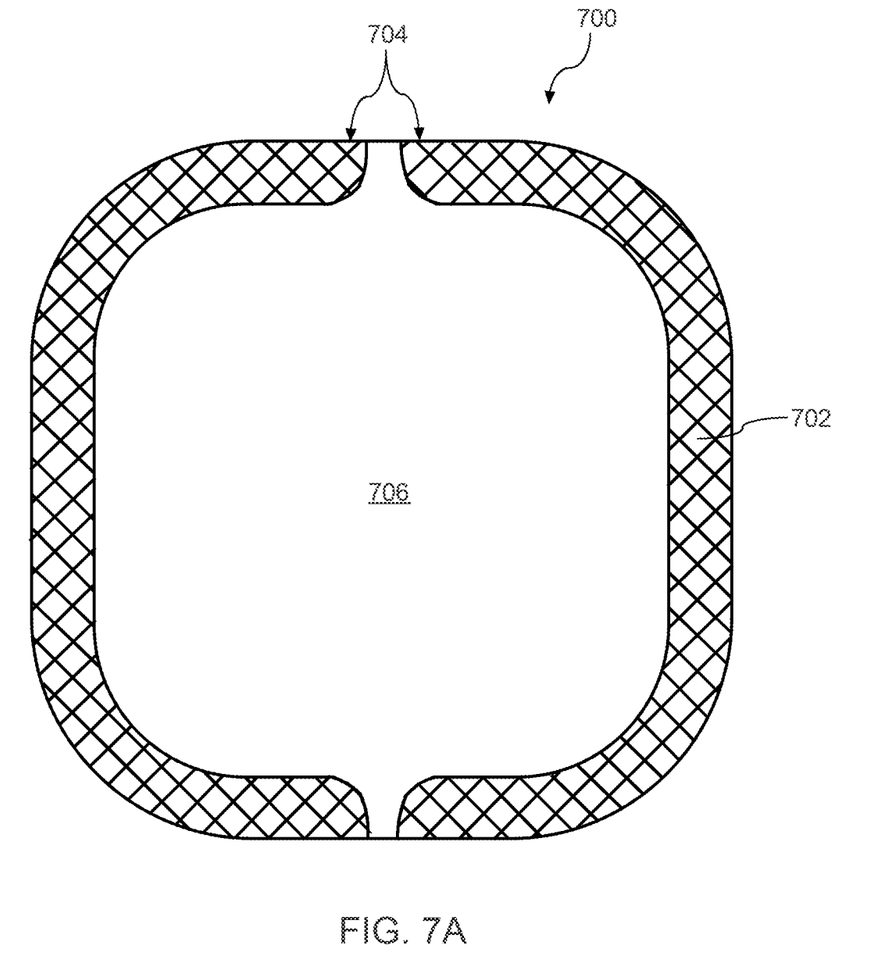
FIG. 7A illustrates a top view of an example, non-limiting outer covering of a wearable computing device according to one or more embodiments of the present disclosure.
Figure 7B:
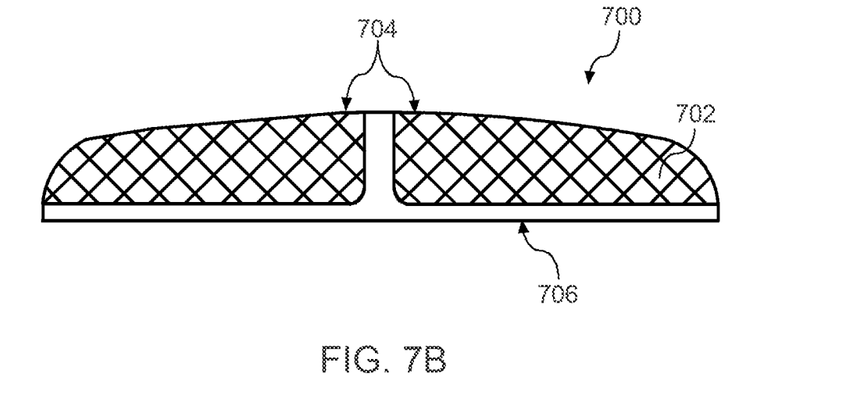
FIG. 7B illustrates a side view of the example, non-limiting outer covering of FIG. 7A.

FIG. 6 illustrates a top view of an example, non-limiting outer covering 600 of a wearable computing device according to one or more embodiments of the present disclosure. As described above, one or more example embodiments of the present disclosure are directed to the use of a removable protective film to form a conductive region such as, for instance, an electrode and/or a sensor on a cover glass of a wearable computing device. For example, in at least one embodiment, a removable protective film can be used to form sensor(s) 112 on outer covering 105 of wearable computing device 100. In this or another embodiment, outer covering 105 illustrated in FIGS. 1 and 3 and outer covering 600 illustrated in FIG. 6 can each constitute a cover glass. In this or another embodiment, outer covering 105 and outer covering 600 can each include the same material, structure, attributes, and/or functionality as that of the other. That is, for instance, in this or another embodiment, outer covering 105 and outer covering 600 can each be constructed of, for example, glass, polycarbonate, acrylic, and/or a similar material. In this or another embodiment, outer covering 600 depicted in FIG. 6 can constitute and/or represent the structure and/or the state of outer covering 600 prior to formation of sensor(s) 112 on outer covering 600. Similarly, in this or another embodiment, outer covering 600 depicted in FIG. 6 can constitute and/or represent the structure and/or the state of outer covering 105 prior to formation of sensor(s) 112 on outer covering 105.

To facilitate formation of sensor(s) 112 on outer covering 600 (and/or outer covering 105) using a removable protective film according to at least one embodiment described herein, a first portion 602 having a first shape and a second portion 604 having a second shape can be defined on a surface (e.g., a top surface) of outer covering 600. For instance, as illustrated in the example embodiment depicted in FIG. 6, first portion 602 can be defined on outer covering 600 such that first portion 602 has a first defined shape that is substantially square with two regions that project away from the center of first portion 602. In this example embodiment, second portion 604 can be defined on outer covering 600 such that second portion 604 has a second defined shape that is substantially U-shaped or channel shaped. In this embodiment, second portion 604 can have a shape that is different from that of first portion 602. In this embodiment, second portion 604 can be proximate to (e.g., adjacent to) first portion 602. The shapes of first portion 602 and second portion 604 depicted in FIG. 6 are illustrative examples, and thus, it should be appreciated that first portion 602 and/or second portion 604 can have different shapes from those shown in FIG. 6 without deviating from the scope of the present disclosure.

In at least one embodiment, to facilitate formation of sensor(s) 112 on outer covering 600 (and/or outer covering 105) using a removable protective film, first portion 602 and second portion 604 can be defined on outer covering 600 using the removable protective film. For example, first portion 602 can be defined on outer covering 600 by: removing (e.g., via cutting) one or more portions of a removable protective film (not shown) to produce a removable protective film element 606 having the first defined shape of first portion 602; and positioning (e.g., adhering, coupling) removable protective film element 606 on outer covering 600 such that removable protective film element 606 defines the first defined shape of first portion 602 of outer covering 600. In the example embodiment depicted in FIG. 6, second portion 604 of outer covering 600 can be defined as a result of the above-described placement (e.g., adhering, coupling) of removable protective film element 606 on outer covering 600 (e.g., the placement of removable protective film element 606 on first portion 602). That is, for instance, by positioning (e.g., adhering, coupling) removable protective film element 606 on outer covering 600 such that removable protective film element 606 defines the first defined shape of first portion 602 of outer covering 600 as described above, second portion 604 can thereby be defined as the area on outer covering 600 that is exposed and/or not covered by removable protective film element 606.

In some embodiments, the above-described removable protective film and/or removable protective film element 606 that can be formed therefrom can include and/or constitute a tape material. For example, the removable protective film and/or removable protective film element 606 can include and/or constitute a polyethylene terephthalate (PET) material layer with an adhesive material layer disposed on a surface of the PET material layer. In these embodiments, the above-described operation of positioning removable protective film element 606 on first portion 602 of outer covering 600 can include coupling the PET material layer of removable protective film element 606 to first portion 602 of outer covering 600 via the adhesive material layer disposed on the surface of the PET material layer of removable protective film element 606.

FIGS. 7A and 7B illustrate a top view and a side view, respectively, of an example, non-limiting outer covering 700 of a wearable computing device according to one or more embodiments of the present disclosure. In the example embodiment depicted in FIGS. 7A and 7B, outer covering 700 can constitute an example, non-limiting alternative embodiment of outer covering 600. For instance, in this example embodiment, outer covering 700 can constitute an example, non-limiting alternative embodiment of outer cover 600 after a material 702 has been deposited on second portion 604 of outer covering 600 and one or more portions of material 702 have been removed to form one or more electrodes 704 as illustrated in FIGS. 7A and 7B. Further, in this example embodiment, outer covering 700 can constitute an example, non-limiting alternative embodiment of outer cover 600 after the partial removal of material 702 as described above and after removal of removable protective film element 606 to yield outer covering 700 having electrode(s) 704 formed thereon and an exposed cover glass portion 706 as illustrated in FIGS. 7A and 7B.

In the example embodiment depicted in FIGS. 7A and 7B, material 702 can include a conductive material such as, for instance, a metal material (e.g., an electrically and/or thermally conductive metal material). In this example embodiment, electrode(s) 704 can constitute sensor(s) 112. That is, for instance, in this or another embodiment, electrode(s) 704 can include the same material, structure, attributes, and/or functionality as that of sensor(s) 112.

To facilitate formation of electrode(s) 704 on outer covering 600 (and/or sensor(s) 112 on outer covering 105) using removable protective film element 606 according to at least one embodiment described herein, material 702 (e.g., a metal material) can be deposited on second portion 604 of outer covering 600. In at least one embodiment, during deposition of material 702 on second portion 604 of outer covering 600, at least a portion of material 702 can also be deposited on at least one surface (e.g., an exposed top surface) of removable protective film element 606, where removable protective film element 606 can be coupled to first portion 602 of outer covering 600 as described above with reference to FIG. 6. In some embodiments, material 702 can be deposited on second portion 604 of outer covering 600 and/or at least one surface of removable protective film element 606 by performing a physical vapor deposition (PVD) process.

In at least one embodiment, based on such deposition of material 702 on second portion 604 of outer covering 600 and/or removable protective film element 606 as described above (e.g., via a PVD process), one or more portions of material 702 can be removed to form electrode(s) 704 illustrated in FIGS. 7A and 7B. In some embodiments, one or more portions of material 702 can be removed by performing, for instance, a grinding process, an etching process (e.g., wet etching, dry etching, laser etching), a polishing process, a cleaning process (e.g., ultrasonic cleaning), and/or another material removal process.

In at least one embodiment, based on such partial removal of material 702 as described above, removable protective film element 606 and a portion of material 702 disposed on removable protective film element 606 can be removed from first portion 602 of outer covering 600 to produce electrode(s) 704 and exposed cover glass portion 706 formed on outer covering 700 as illustrated in FIGS. 7A and 7B. For example, in some embodiments, removable protective film element 606 and any material 702 deposited on a top surface of removable protective film element 606 can be removed from first portion 602 of outer covering 600 by performing, for instance, a peeling process, a polishing process, a cleaning process, and/or another material removal process. In embodiments where removable protective film element 606 includes a PET material layer with an adhesive material layer coupled thereto as described above, the PET material layer, the adhesive material layer, and/or any material 702 deposited on a top surface of the PET material layer can be removed from first portion 602 of outer covering 600. For example, in these embodiments, the PET material layer, the adhesive material layer, and/or any material 702 deposited on a top surface of the PET material layer can be removed from first portion 602 of outer covering 600 by performing, for instance, a peeling process, a polishing process, a cleaning process, and/or another material removal process. In these embodiments, the PET material layer and/or the adhesive material layer can be removed from first portion 602 of outer covering 600 such that neither of these materials and/or residue thereof remain on exposed cover glass portion 706 of outer covering 700.

In one or more embodiments, the above-described fabrication operations can be performed in a manner such that when removable protective film element 606 is removed from first portion 602, at least one of outer covering 700, electrode(s) 704, and/or exposed cover glass portion 706 can have one or more defined attributes. For example, the above-described fabrication operations can be performed such that outer covering 700, electrode(s) 704, and/or exposed cover glass portion 706 can each have a certain dimension, a certain profile (e.g., curved, sloped), a certain geometry (e.g., U-shaped, channel shaped), one or more certain edges (e.g., rounded edge(s), flat edge(s)), a certain location (e.g., a certain location of the electrode relative to the cover glass), a certain aesthetic feature (e.g., color, reflection intensity, texture, finish), and/or another defined attribute. For instance, electrode(s) 704 can have a curved and/or sloped profile with rounded edges at the periphery of outer covering 700 and at least one flat, vertical edge at the interface of electrode(s) 704 and exposed cover glass portion 706. In another example, exposed cover glass portion 706 can have a certain degree of transparency (e.g., a relatively high degree of transparency) that satisfies a certain design criterion. In another example, the top surface of exposed cover glass portion 706 can be free of any adhesive material from the adhesive material layer of removable protective film element 606 that was previously coupled to first portion 602 of outer covering 600.

Although not illustrated in FIG. 6, 7A, or 7B, in some embodiments, electrode(s) 704 can be formed on outer covering 700 in a similar or same manner as sensor(s) 112 can be formed on outer covering 105, where sensor(s) 112 are at least partially disposed on outer covering 105 and dorsal wrist-side face 110 as illustrated in FIGS. 1 and 2. That is, for instance, one or more vias (e.g., holes, tunnels) can be formed (e.g., using an etching process) through outer covering 600 such that material 702 can be deposited (e.g., using a PVD process) in the one or more vias to form electrode(s) 704 such that electrode(s) 704 can be at least partially disposed on outer covering 700 as illustrated in FIGS. 7A and 7B and at least partially disposed on dorsal wrist-side face 110 of wearable computing device 100. In additional or alternative embodiments, electrode(s) 704 can be formed on outer covering 700 such that electrode(s) 704 can be coupled to at least one controller(s) 202 described above with reference to FIG. 2.

In at least one example embodiment, based on such formation of electrode(s) 704 and exposed cover glass portion 706 on outer covering 700 as described above with reference to FIGS. 6, 7A, and 7B, outer covering 700 can thereby constitute a cover glass having a first removable film defined portion and a second removable film defined portion. That is, for instance, in this or another embodiment, outer covering 700 can constitute a cover glass having a first removable film defined portion such as, for example, first portion 602 and a second removable film defined portion such as, for instance, second portion 604 that can each be defined using removable protective film element 606 as described above. In this or another embodiment, electrode(s) 704 can be formed such that electrode(s) 704 are disposed on such a second removable film defined portion of outer covering 700 (e.g., on second portion 604). In embodiments where electrode(s) 704 can be formed on outer covering 700 such that electrode(s) 704 can be coupled to at least one controller(s) 202, electrode(s) 704 can be formed such that electrode(s) 704 are disposed on such a second removable film defined portion of outer covering 700 (e.g., on second portion 604) and are coupled to the at least one controller(s) 202. In these or other embodiments, the above-described fabrication operations can be performed in a manner such that outer covering 700, electrode(s) 704, and/or exposed cover glass portion 706 can have one or more defined attributes (e.g., one or more of the attributes defined above).

Figure 8:
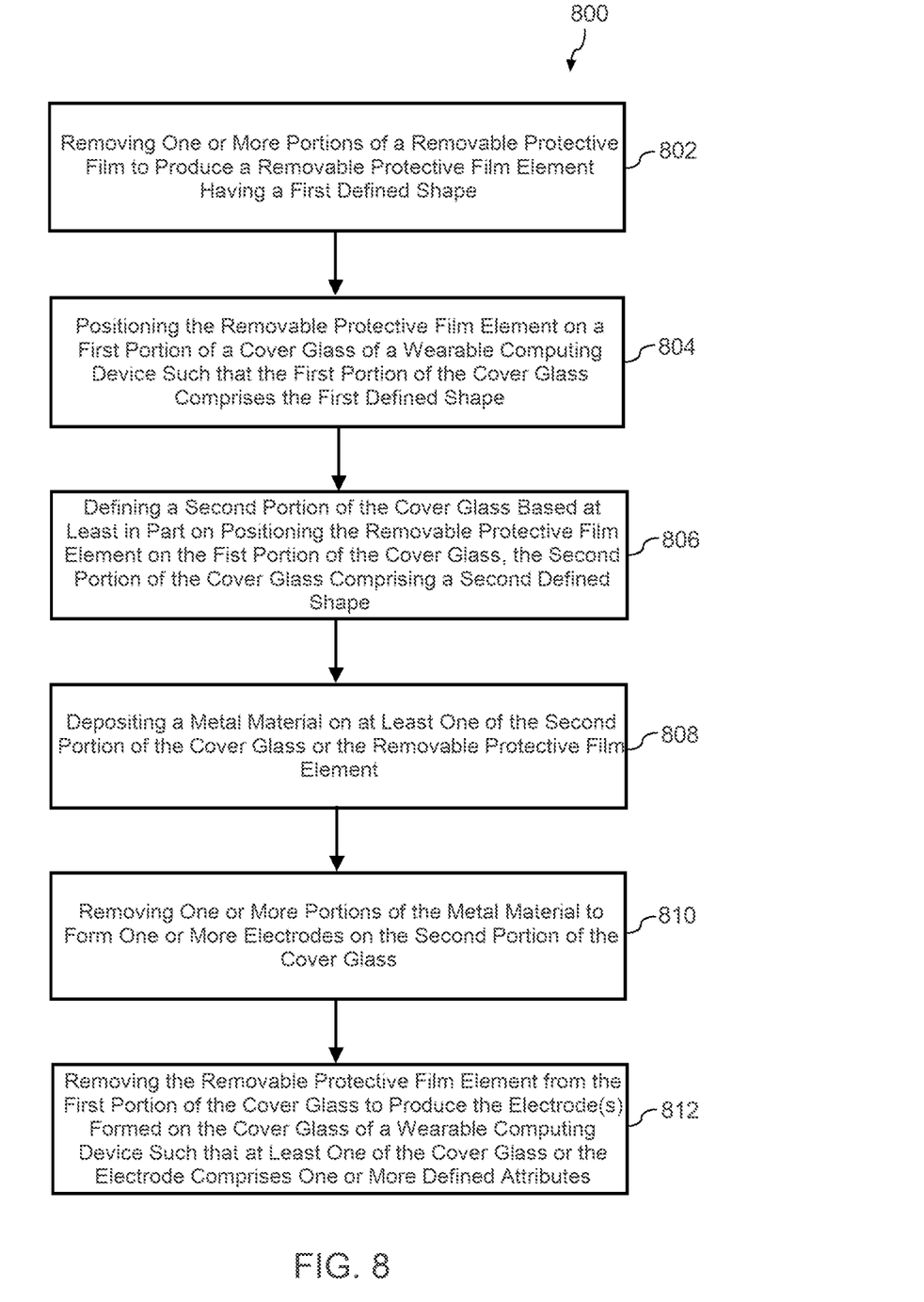
FIGS. 8 and 9 each illustrate a flow diagram of an example, non-limiting method that can be implemented to use a removable protection film to form an electrode on a cover glass of a wearable computing device according to one or more embodiments of the present disclosure.

FIG. 8 illustrates a flow diagram of an example, non-limiting method 800 that can be implemented to use a removable protective film to form an electrode on a cover glass of a wearable computing device according to one or more embodiments of the present disclosure. Method 800 can be implemented using, for instance, fabrication equipment that can facilitate formation of a conductive region on a cover glass of a wearable computing device (e.g., fabrication equipment used to fabricate integrated circuits and/or semiconductor devices). In some embodiments, method 800 can be implemented using, for instance, a computing system that can be coupled (e.g., communicatively, electrically, operatively) to such fabrication equipment. In these embodiments, such a computing system can include one or more processors and one or more non-transitory computer-readable storage media that can include instructions that, when executed by the one or more processors, can cause the computing system and/or the fabrication equipment to perform one or more operations of method 800. The example embodiment illustrated in FIG. 8 depicts operations performed in a particular order for purposes of illustration and discussion. Those of ordinary skill in the art, using the disclosures provided herein, will understand that various operations or steps of method 800 or any of the other methods disclosed herein can be adapted, modified, rearranged, performed simultaneously, removed, include operations not illustrated, and/or modified in various ways without deviating from the scope of the present disclosure.

At 802, method 800 can include removing one or more portions of a removable protective film (e.g., a PET tape) to produce a removable protective film element (e.g., removable protective film element 606) having a first defined shape (e.g., a substantially square or rectangular shape).

At 804, method 800 can include positioning (e.g., adhering, coupling) the removable protective film element on a first portion (e.g., first portion 602) of a cover glass (e.g., outer covering 600) of a wearable computing device (e.g., wearable computing device 100) such that the first portion of the cover glass has the first defined shape.

At 806, method 800 can include defining a second portion (e.g., second portion 604) of the cover glass based at least in part on positioning the removable protective film element on the first portion of the cover glass, the second portion of the cover glass having a second defined shape (e.g., substantially U-shaped or channel shaped).

At 808, method 800 can include depositing (e.g., via a PVD process) a metal material (e.g., an electrically and/or thermally conductive metal material) on at least one of the second portion of the cover glass or the removable protective film element.

At 810, method 800 can include removing (e.g., via grinding, etching, polishing process, cleaning) one or more portions of the metal material to form one or more electrodes (e.g., electrode(s) 704) on the second portion of the cover glass.

At 812, method 800 can include removing (e.g., via peeling, polishing, cleaning) the removable protective film element (e.g., removing removable protective film element 606 and/or any material 702 deposited on a top surface of removable protective film element 606) from the first portion of the cover glass to produce the electrode(s) formed on the cover glass of a wearable computing device (e.g., wearable computing device 100) such that at least one of the cover glass or the electrode has one or more defined attributes (e.g., one or more of the attributes defined above with reference to FIGS. 7A and 7B).

Figure 9:
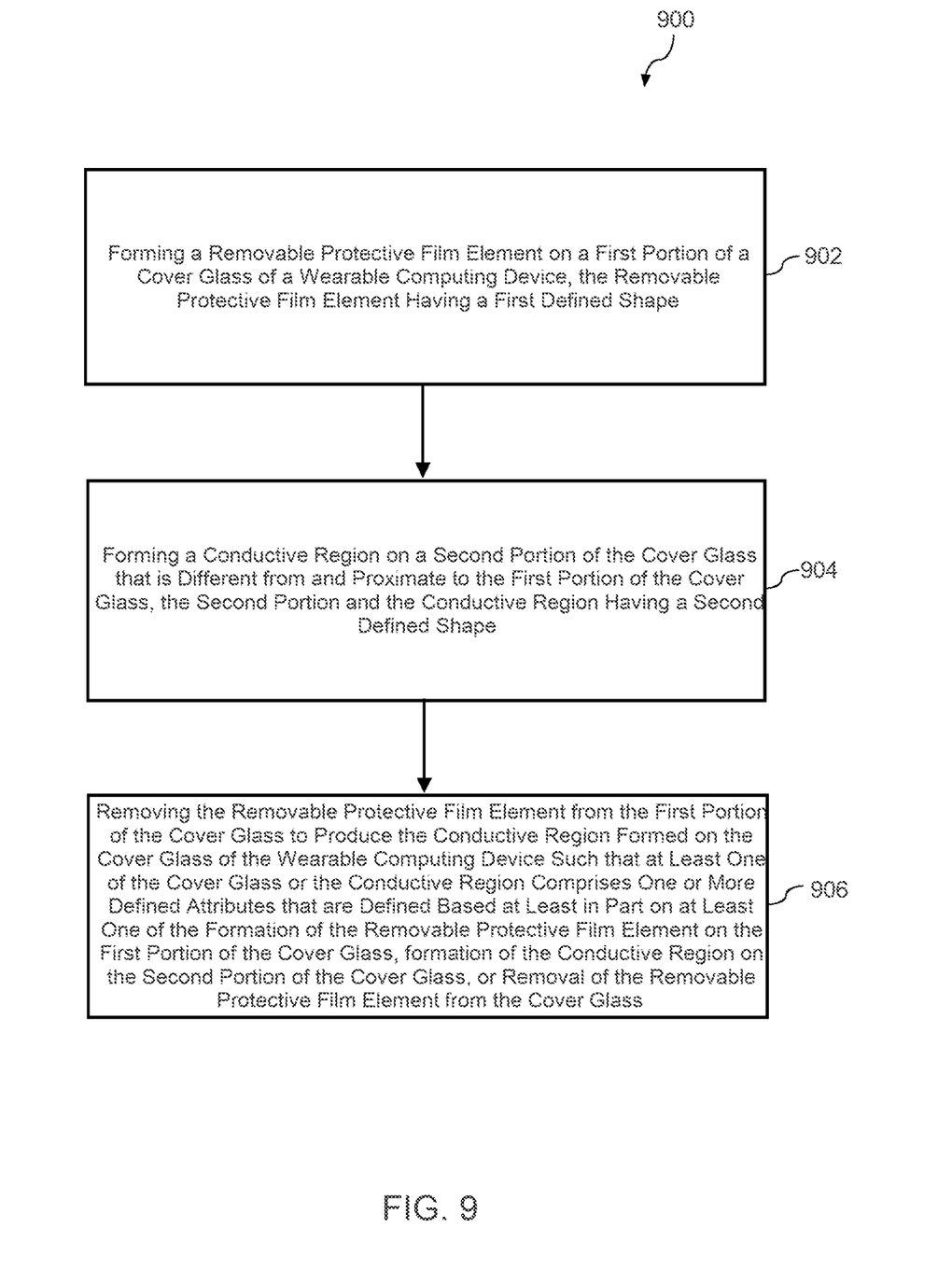

FIG. 9 illustrates a flow diagram of an example, non-limiting method 900 that can be implemented to use a removable protective film to form an electrode on a cover glass of a wearable computing device according to one or more embodiments of the present disclosure. Method 900 can be implemented using, for instance, fabrication equipment that can facilitate formation of a conductive region on a cover glass of a wearable computing device (e.g., fabrication equipment used to fabricate integrated circuits and/or semiconductor devices). In some embodiments, method 900 can be implemented using, for instance, a computing system that can be coupled (e.g., communicatively, electrically, operatively) to such fabrication equipment. In these embodiments, such a computing system can include one or more processors and one or more non-transitory computer-readable storage media that can include instructions that, when executed by the one or more processors, can cause the computing system and/or the fabrication equipment to perform one or more operations of method 900. The example embodiment illustrated in FIG. 9 depicts operations performed in a particular order for purposes of illustration and discussion. Those of ordinary skill in the art, using the disclosures provided herein, will understand that various operations or steps of method 900 or any of the other methods disclosed herein can be adapted, modified, rearranged, performed simultaneously, removed, include operations not illustrated, and/or modified in various ways without deviating from the scope of the present disclosure.

At 902, method 900 can include forming (e.g., as described above with reference to FIG. 6) a removable protective film element (e.g., removable protective film element 606) on a first portion (e.g., first portion 602) of a cover glass (e.g., outer covering 600) of a wearable computing device (e.g., wearable computing device 100), the removable protective film element having a first defined shape (e.g., a substantially square or rectangular shape).

At 904, method 900 can include forming (e.g., as described above with reference to FIGS. 6, 7A, and 7B) a conductive region (e.g., electrode(s) 704) on a second portion (e.g., second portion 604) of the cover glass that is different from and proximate to the first portion of the cover glass, the second portion and the conductive region having a second defined shape (e.g., substantially U-shaped or channel shaped).

At 906, method 900 can include removing (e.g., via peeling, polishing, cleaning) the removable protective film element (e.g., removing removable protective film element 606 and/or any material 702 deposited on a top surface of removable protective film element 606) from the first portion of the cover glass to produce the conductive region formed on the cover glass of the wearable computing device such that at least one of the cover glass or the conductive region has one or more defined attributes (e.g., one or more of the attributes defined above with reference to FIGS. 7A and 7B) that are defined based at least in part on at least one of formation of the removable protective film element on the first portion of the cover glass, formation of the conductive region on the second portion of the cover glass, or removal of the removable protective film element from the cover glass.

Additional Disclosure

The technology discussed herein makes reference to servers, databases, software applications, and other computer-based systems, as well as actions performed by, and information sent to and from such systems. The inherent flexibility of computer-based systems allows for a great variety of possible configurations, combinations, and divisions of tasks and functionality between and among components. For instance, processes discussed herein can be implemented using a single device or component or multiple devices or components working in combination. Databases and applications can be implemented on a single system or distributed across multiple systems. Distributed components can operate sequentially or in parallel.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure covers such alterations, variations, and equivalents.

What is claimed is:

1. A method to form an electrode on a cover glass of a wearable computing device, the method comprising:
- providing the cover glass of the wearable computing device, wherein the cover glass includes a first portion and a second portion;
- providing a removable protective film, wherein the removable protective film includes one or more portions;
- forming a removable protective film element having a first defined shape and a second defined shape by removing the one or more portions of the removable protective film;
- positioning the removable protective film element on the first portion of the cover glass of the wearable computing device such that the first portion of the cover glass is configured to match the first defined shape;
- defining and forming the second portion of the cover glass of the wearable computing device while the removable protective film element is positioned on the first portion of the cover glass of the wearable computing device, the second portion formed of the cover glass configured to match the second defined shape of the removable protective film element;
- depositing a metal material on the second portion of the cover glass;
- removing one or more portions of the metal material to form the electrode on the second portion of the cover glass; and
- removing the removable protective film element from the first portion of the cover glass to produce the electrode formed on the cover glass of the wearable computing device such that the electrode formed on the cover glass comprises one or more defined attributes.

2. The method of claim 1, wherein the removable protective film element is a polyethylene terephthalate material layer.

3. The method of claim 2, wherein the positioning the removable protective film element on the first portion of the cover glass comprises:
- coupling the polyethylene terephthalate material layer to the first portion of the cover glass, the polyethylene terephthalate material layer being coupled to the first portion of the cover glass via an adhesive material layer disposed on a surface of the polyethylene terephthalate material layer.

4. The method of claim 2, wherein the removing the removable protective film element from the first portion of the cover glass comprises:
- removing the polyethylene terephthalate material layer from the first portion of the cover glass.

5. The method of claim 2, wherein the removing the removable protective film element from the first portion of the cover glass comprises:
- performing at least one of a peeling process, a polishing process, or a cleaning process to remove the polyethylene terephthalate material layer from the first portion of the cover glass.

6. The method of claim 1, wherein the depositing the metal material on at least one of the second portion of the cover glass or the removable protective film element comprises:
- performing a physical vapor deposition process to deposit the metal material on at least one of the second portion of the cover glass or the removable protective film element.

7. The method of claim 1, wherein the removing the one or more portions of the metal material comprises:
- performing at least one of a grinding process, an etching process, a polishing process, or a cleaning process to remove the one or more portions of the metal material.

8. The method of claim 1, wherein the removing the removable protective film element from the first portion of the cover glass comprises:
- performing at least one of a peeling process, a polishing process, or a cleaning process to remove the removable protective film element and a defined amount of the metal material disposed on the removable protective film element from the first portion of the cover glass.

9. The method of claim 1, wherein the one or more defined attributes comprise at least one of a defined dimension, a defined profile, a defined geometry, a defined edge, a defined location, or a defined aesthetic feature of at least one of the cover glass or the electrode.

10. The method of claim 1, wherein the wearable computing device comprises at least one of a smartwatch, a personal health monitoring device, a biometric tracking device, a biometric monitoring device, a heart monitor, or a fitness tracker.

11. The method of claim 1, wherein the electrode formed on the cover glass of the wearable computing device comprises at least one of a sensor, a biometric sensor, a fingerprint sensor, a temperature sensor, a humidity sensor, a light sensor, a pressure sensor, an image sensor, a microphone, a photoplethysmogram sensor, or an electrodermal activity sensor.

* * * * *